United States Patent [19]

Dick et al.

[11] 4,232,023
[45] Nov. 4, 1980

[54] NOVEL SOLUBLE DERIVATIVES OF 2,4-DIAMINO PYRIMIDINE

[76] Inventors: Pierre R. Dick, Villa "Sama Keur" 95, Ave. de la Lanterne 06; Max Rombi, 67, Rue Rossini 06, both of Nice, France

[21] Appl. No.: 922,845

[22] Filed: Jul. 7, 1978

[30] Foreign Application Priority Data

Jul. 11, 1977 [FR] France .................. 77 22323

[51] Int. Cl.³ .................. A61K 31/505; C07D 239/49
[52] U.S. Cl. .................. 424/251; 424/180; 536/54; 544/325; 542/425
[58] Field of Search .................. 544/325; 536/54; 424/251; 542/425

[56] References Cited

U.S. PATENT DOCUMENTS 3,111,521  11/1963  Hoefle et al. .................. 544/325

OTHER PUBLICATIONS

Stogryn, J. Medicinal Chem., 1973, vol. 16, No. 12, pp. 1399–1401.

Primary Examiner—Paul M. Coughlan, Jr.
Attorney, Agent, or Firm—Cushman, Darby & Cushman

[57] ABSTRACT

The novel derivatives correspond to the general formula II:

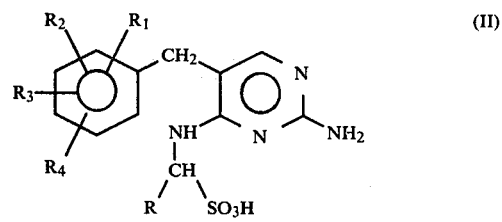

in which: $R_1$ $R_2$ $R_3$ and $R_4$ represent identical or different groups which can each be a hydrogen or halogen atom or an alkyl group, alkoxy, or benzyloxy group and R is the residue of an R—CHO aldehyde selected from among linear or branched saturated aliphatic aldehydes including 1 to 4 carbon atoms or again represents the Z—CH=CH radical in which Z represents a hydrogen atom, a linear or branched saturated alkyl group, an aromatic nucleus or an aromatic heterocyclic nucleus or again R represents the radical HO $CH_2$ (CH OH)$_n$—in which n has the value of 3 or 4. The novel compounds have high solubility in water and antibacterial activity and potentiating power.

15 Claims, No Drawings

NOVEL SOLUBLE DERIVATIVES OF 2,4-DIAMINO PYRIMIDINE

BACKGROUND OF THE INVENTION

1. Field of the Invention

The invention relates to a novel soluble derivatives of 2,4-diamino-5-benzyl-pyrimidine.

2. Description of the Prior Art

In French Patent Application No. 76 22 162, there are mentioned novel derivatives of 2,4-diamino-pyrimidine obtained by substituting hydrogen atoms of the amine functions by sodium sulfonate groups. More particularly, the products described therein correspond to the following formula:

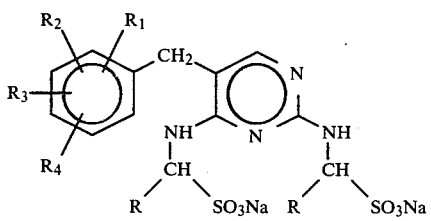

in which the symbols $R_1$, $R_2$, $R_3$, $R_4$ represent identical and/or different groups which can each be a hydrogen or a halogen atom, or an alkyl, alkoxy, or benzyloxy group and the symbol R corresponds to the residue of an aldehyde function selected either from among linear or branched saturated aliphatic aldehydes including 1 to 4 carbon atoms, or unsaturated aliphatic aldehydes of the vinyl type, substituted at the alpha postion of the ethylene bond of the formula Z—CH=CH—CHO, in which Z corresponds to hydrogen, to linear or branched saturated alkyl groups, or to aromatic nuclei, or polyhydroxylated aldehydes of the formula HO CH$_2$—(CH OH)n—CHO where n takes the value 3 or 4.

These novel products have the same pharmaceutical and therapeutic properties as the basic 2,4-diamino pyrimidines and are used as bactericidal activity potentiators of the sulfamides with which they are associated.

According to the teachings of French Patent Application No. 76 22 162, the starting materials (2,4-diamino-5-benzyl-pyrimidines), subjected to the action of a bisulfite compound or of the mixture aldehyde+sodium bisulfite, lead to disubstituted products.

As indicated in this patent application, the disubstituted derivatives have the double advantage of high solubility in water, whilst preserving the potentiating power and the antibacterial activity of the starting compounds.

However, these compounds, by reason of their double substitution, have a relatively high molecular weight.

It is an object of the invention consequently to provide derivatives of 2,4-diamino-5-benzyl-pyrimidine having the same therapeutic and water solubility water properties as the compounds according to Patent Application No. 76 22 162 but with a lower molecular weight.

It is another object of the invention to provide a process for producing such improved derivatives of 2,4-diamino-5-benzyl-pyrimidines.

GENERAL DESCRIPTION OF THE INVENTION

According to the invention this purpose is achieved by preparing novel monosubstituted derivatives from the starting diaminopyrimidines.

Applicants have in fact been able to establish that, surprisingly, the reactivity of the two amine functions of the pyrimidinic nucleus is substantially different and that with respect to certain reactants and under particular reaction conditions, it is possible to carry out the substitution on one of the functions without affecting the second. More precisely, it has been found that the amino function located at the 4 position on the pyrimidine nucleus is more reactive than that located at the 2 position.

The novel derivatives according to the invention correspond to the following general formula II:

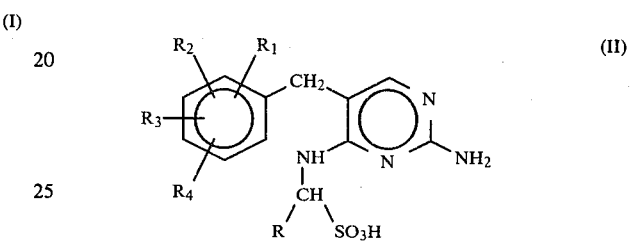

in which the symbols $R_1$, $R_2$, $R_3$, $R_4$ represent the groups previously described and R belongs to the three aforementioned aldehyde catagories. These novel derivatives may be obtained either in the form of a free sulfonic acid or in the form of an alkali metal salt (e.g. of sodium or potassium).

Among the compounds corresponding to the general formula II, there may be mentioned in particular 2,4-diamino-5-(3',4',5'-trimethoxybenzyl)pyrimidine N$_4$ ethane sulfonic acid or TRIMETHOPRIME ETHANE SULFONIC acid, 2,4-diamino-5-(3',4'-dimethoxybenzyl)pyrimidine N$_4$ methane sulfonic acid or DIAVERIDINE methane sulfonic acid; 2,4-diamino, 5-(2'methyl, 4',5'-dimethoxybenzyl)pyrimidine N$_4$ isobutane sulfonic acid or ORMETHOPRIME isopropane sulfonic acid; 2,4-diamino, 5-(3',4',5'-trimethoxybenzyl)pyrimidine N$_4$ glucose sulfonic acid or TRIMETHOPRIME glucose sulfonic acid; 2,4-diamino, 5-(3',4',5'-trimethoxybenzyl)-pyrimidine N$_4$ methane sulfonic acid or TRIMETOPRIME METHANE SULFONIC acid.

The preparation of these derivatives can be carried out according to the procedure described in the aforementioned French Patent Application No. 76 22 162, that is to say by reacting the selected aldehyde in the form of its bisulfite compound, or again by reacting simultaneously the aldehyde and the sodium bisulfite, the amount of reactants utilized being stoichiometric and corresponding to the production of the monosubstituted product.

The experimental conditions relating to the time and reflux temperature are much gentler than for producing the disubstituted derivatives. Thus the reaction can be conducted for 12 hours but working at room temperature or slightly above.

On the other hand, the nature of the solvents only very slightly influences the substitution and they are those utilized and indicated in the abovementioned patent applicaton. The extraction of the product formed (that is to say the sodium salt) is carried out either directly by spraying or by the usual separation techniques. According to the methods used one or several purifications are sometimes necessary.

A modification consists of reacting the 2,4-diamino benzyl pyrimidine with the selected aldehyde and introducing the sulfonic function by bubbling sulfur dioxide into the reaction medium. This modification permits the production of the sulfonic derivative in a remarkably pure condition and among other things avoiding formation of inorganic sulfite derivatives which are very difficult to eliminate subsequently; moreover when the reaction is carried out in an alcoholic solvent, the sulfonic acid derivative precipitates in the cold, which facilitates the steps of separation and purification.

The Examples 1 to 3, which are not to be considered as in any way limiting, serve to illustrate the techniques of producing these novel derivatives.

The products obtained according to the present invention are in all points comparable with the derivative according to French Patent Application No. 76 22 162, both from the point of view of their solubility and from that of their therapeutic properties.

The monosubstituted derivatives obtained in the form of sodium salt are soluble in water to concentrations going up to 20% by weight and the pH value of such solutions is close to neutral. The acid forms are solubilized in alkaline aqueous solutions to give solutions identical with the sodium forms.

From the pharmacological point of view, all the properties inherent in the disubstituted derivatives reoccur in the monosubstituted derivatives. The toxicological properties (LD 50, tolerance) are quite similar whilst the antibacterial and potentiating expressed per gram of product is about 20% higher.

This increase in therapeutic activity permits the preparation of medicaments containing a smaller amount of active principle. It is self-evident that this contributes a practical advantage and an economic interest which are not negligible.

These novel monosubstituted potentiators can also be associated with a soluble derivative of sulfamide to lead to an injectable or oral pharmaceutical preparation in the form of a stable and neutral solution. The therapeutic performances of these pharmaceutical preparations are in every way comparable with those described in French Patent Application No. FR 76 22 162. Examples 4 and 5, only constitute, of course, non-limiting illustrations of the administrable pharmaceutical forms.

DESCRIPTION OF PREFERRED EMBODIMENTS

EXAMPLE 1

2,4-diamino5-(3',4'5'-trimethoxybenzyl)pyrimidine sodium $N_4$ ethane sulfonate or sodium Trimethoprime ethane sulfonate.

Into a one liter reaction vessel provided with a mechanical stirrer, with efficient water cooling of the Dimroth type, with a bromine funnel with equalization of pressure, with a temperature detector and a heating jacket, are introduced 58 g of Trimethoprime (about 0.2 Mole) in 500 ml of softened water. The suspension is brought without stirring to about 60° C. and then drop-by-drop 31 g (0.21 Mole) of the acetaldehyde bysulfite compound is added. The temperature of the mixture is maintained at 60° for two hours after the addition and then it is left to stand overnight. The suspension is filtered and concentrated under vacuum with a rotary evaporator for the filtrate. The slurry obtained is concentrated to dryness by azeotropic evaporation with benzene and then with acetone. A microcrystalline powder, white in color, results.

Purity checks by thin layer chromatography (support: glass plate coated with a silicate gel with a fluorescence indicator).

Eluants: Chloroform-Methanol-Water 48-18-4.

Development: UV lamp 254 nm, causes a slight rf spot close to 0.8 to appear corresponding to the starting Trimethoprime and a large rf spot close to 0.65 corresponding to the monosubstituted derivative formed.

After purification with a mixture of absolute ethanol-/ethyl acetate 50—50, a 98% pure product is obtained which melts towards 170° C.

Study of the infra-red, NMR and ultraviolet spectra confirm the structure of the product.

The percentage analysis corresponding to the empirical formula: $C_{16}H_{21}N_4O_6SNa$ gives the following results: Theory: C%: 45.39-H%: 4.96-N%: 13.23-S%: 7.56 Na%: 5.43. Found: C%: 45.1-H%: 5.1-N%: 13.0-S%: 7.9-Na%: 5.5.

EXAMPLE 2

Sodium $N_4$ methane sulfonate of 2,4-diamino-5(3',4'-dimethoxybenzyl)pyrimidine or sodium diaveridine methane sulfonate.

In the same apparatuss as described in Example 1, 0.2 Mole, namely 52 g of diaveridine suspended in 350 ml of water was introduced, the suspension is heated to about 60° C. and then without stirring, 200 ml of an aqueous solution was added containing 29.1 g namely 0.21 M of the bisulfite compound of formaldehyde. After stirring for one hour at about 60° C., the mixture was allowed to stand for 12 hours at room temperature.

The suspension was filtered so as to remove the unreacted portion of diaverine and the solution was concentrated under vacuum.

After extraction and purification, the powder obtained was checked by thin layer chromatography. IR, UV and NMR analyses confirmed the structure of the product formed.

Percentage analysis results correspond to the empirical formula: $C_{14}H_{17}N_4O_5SNa$, and were as follows: Theory: C%: 44.68-H%: 4.52-N%: 14.89-S%: 8.51Na%: 6.11. Found: C%: 44.3-H%: 4.9%-N%: 14.7-S%: 9.0Na%: 6.3.

EXAMPLE 3

$N_4$ ethane sulfonic acid of 2,4-diamino-5-(3',4',5'-trimethoxybenzyl)pyrimidine or trimethoprime ethane sulfonic acid In a reaction vessel of 1 liter capacity equiped as in the previous examples, were dissolved in 400 ml of 95° ethanol GL.58 g namely (0.2 Mole) of Trimethoprime, then 11 g of ethanol namely 0.25 mole was added. It was stirred and the temperature of the mixture brought to 35°-40° C. After 30 minutes sulfur dioxide was bubbled into the mixture for 90 minutes. The solution was brought to reflux and kept thereat for an hour. The mixture was allowed to cool and to stand at least over night at +2° C. The suspension obtained was filtered. The powder dried and analysed by TLC corresponds to the expected product with a percentage purity of about 99%. The IR, UV and NMR spectra were in agreement and confirmed the structure of the product.

EXAMPLE 4

Injectable solution

Preparation of a solution containing the following substances:

| | |
|---|---|
| Sodium trimethoprime ethane sulfonate (namely 2 g of trimethoprime base) | 2.91 g |
| Sodium sulfamethoxypyridazine bis ethane sulfonate (namely 10 g of sulfamethoxypyridazine base) | 19.3 g |
| Disodium ethylene diamine tetraacetate | 0.1 g |
| Methyl sodium parahydroxybenzoate | 0.1 g |
| Water for injection | q.s.p. 100 ml |

Into half the final volume of water, is dissolved the preservative agent and the complexing agent, and then the two active principles were introduced in the cold and without stirring. After complete dissolution, the final volume was adjusted with water. The final pH was 6.5±0.3.

The sterility of the solution was achieved by filtration.

EXAMPLE 5

Injectable solution

Preparation of the solution containing the following substances:

| | |
|---|---|
| Trimethoprime ethane sulfonic acid (namely 2 g of Trimethoprime base) | 2.75 g |
| Sodium sulfamethoxazole ethane sulfonate (namely 10 g of base) | 20.2 g |
| Disodium ethylene diamine tetraacetate | 0.1 g |
| Methyl sodium parahydroxybenzoate | 0.09 g |
| Propyl sodium parahydroxybenzoate | 0.01 g |
| N solution of sodium hydroxide | q.s.p. pH 7 |
| Water for injectable preparation | q.s.p. 100 ml |

The procedure was as in the preceding example. However the pH was adjusted to 7 with a quantity of normal solution of sodium hydroxide before completing it to the final volume.

We claim:

1. Derivatives of 2,4-diamino pyrimidine corresponding to the general formula II:

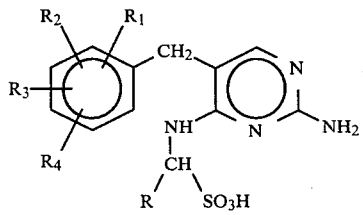

in which:
- $R_1$, $R_2$, $R_3$ and $R_4$ independently represent a hydrogen atom, a halogen atom, a methyl group, a methoxy group or a benzyloxy group; and,
- R is the radical of a R—CHO aldehyde wherein R represents hydrogen or an alkyl group containing from 1 to 3 carbon atoms, the Z—CH=CH radical wherein Z represents a hydrogen atom or a benzene ring; or
- R represents the radical HO—CH$_2$—(CHOH)$_n$— in which n has the value 3 or 4.

2. Derivatives of 2,4-diamino pyrimidine according to claim 1, wherein Z represents a benzene ring.

3. Derivatives of 2,4-diamino pyrimidine selected from the group consisting of 2,4-diamino-5-(3',4',5'-trimethoxybenzyl)pyrimidine $N_4$ ethane sulfonic acid (or its sodium salt); 2,4-diamino-5-(3',4',5'-trimethoxybenzyl)pyrimidine $N_4$ methane sulfonic acid (or its sodium salt); 2,4-diamino-5-(3',4',5'-trimethoxybenzyl)pyrimidine $N_4$ glucose sulfonic acid (or its sodium salt); 2,4-diamino-5-(3',4'-dimethoxybenzyl)pyrimidine $N_4$ ethane sulfonic acid (or its sodium salt); 2,4-diamino-5-(3',4'-dimethoxybenzyl)pyrimidine $N_4$ glucose sulfonic acid (or its sodium salt); 2,4-diamino-5-(3',4'-dimethoxybenzyl)pyrimidine methane sulfonic acid (or its sodium salt); 2,4-diamino-5-(2'-methyl-4',5'-dimethoxybenzyl)pyrimidine $N_4$ methane sulfonic acid (or its sodium salt) and 2,4-diamino-5-(2'-methyl-4',5'-dimethoxybenzyl)pyrimidine $N_4$ isobutane sulfonic acid (or its sodium salt).

4. An antibacterial medicament, comprising as active principle a pharmacologically effective amount of, at least one compound according to claim 1.

5. Antibacterial medicament comprising as its active principle a pharmacologically effective amount of, at least one compound according to claim 3.

6. Antibacterial medicament in the form of an aqueous solution with a pH in the vicinity of neutrality including as active principle a pharmacologically effective amount of at least one derivative of 2,4-diamino pyrimidine according to claim 1, associated with a soluble derivative of sulfamide selected from among sodium alkane sulfonates and sodium polyhydroxysulfonates.

7. Antibacterial medicament in the form of an aqueous solution with a pH in the vicinity of neutrality including as active principle a pharmacologically effective amount of at least one derivative of 2,4-diamino pyrimidine according to claim 2, associated with a soluble derivative of sulfamide selected from among sodium alkane sulfonates and sodium polyhydroxysulfonates.

8. Antibacterial medicament according to claim 6, comprising between 1 and 50% by weight of active principles and a ratio by weight between the soluble derivative of sulfamide and the derivative of 2,4-diamino pyrimidine comprised between 20 and 0.1.

9. Antibacterial medicament according to claim 7, comprising between 1 and 50% by weight of active principle and a ratio by weight betwen the soluble derivative of sulfamide and th derivative of 2,4-diamino pyrimidine comprised between 20 and 0.1.

10. Antibacterial medicament according to claim 6, in the form of a pharmaceutical composition permitting parenteral and/or oral administration in humans and animals.

11. Antibacterial medicament according to claim 7, in the form of a pharmaceutical composition enabling parenteral and/or oral administration in humans and animals.

12. Antibacterial medicament according to claim 8, in the form of a pharmaceutical composition enabling parenteral and/or oral administration in humans and animals.

13. Antibacterial medicament according to claim 9, in the form of a pharmaceutical composition enabling parenteral and/or oral administration in humans and animals.

14. Method of treating humans or animals suffering from bacterial infections, comprising administering a pharmacologically effective amount of a compound according to claim 1.

15. Method of treating humans or animals suffering from bacterial infections, comprising administering a pharmacologically effective amount of a compound according to claim 2.

* * * * *